United States Patent [19]

Kruse

[11] 4,173,514
[45] Nov. 6, 1979

[54] HIGH MANNITOL PROCESS (ENZYMATIC ISOMERIZATION)

[75] Inventor: Walter M. Kruse, Wilmington, Del.

[73] Assignee: ICI Americas Inc., Wilmington, Del.

[21] Appl. No.: 802,653

[22] Filed: Jun. 2, 1977

[51] Int. Cl.$^2$ ............................................. C12D 13/02
[52] U.S. Cl. ......................................................... 435/94
[58] Field of Search ................... 127/46 A; 195/31 F, 195/31 R, 12; 260/635 C; 536/1

[56] References Cited

U.S. PATENT DOCUMENTS

| Re. 29,130 | 2/1977 | Lee et al. | 195/31 F |
|---|---|---|---|
| Re. 29,136 | 2/1977 | Long | 195/31 F |
| 2,759,024 | 8/1956 | Kaschagen | 260/635 C |
| 2,950,228 | 8/1960 | Marshall | 195/66 |
| 3,329,729 | 7/1967 | Brandner et al. | 260/635 C |
| 3,632,656 | 1/1972 | Unver | 260/635 R |
| 3,645,848 | 2/1972 | Lee et al. | 195/31 F |
| 3,705,199 | 12/1972 | deBerardinis | 260/635 R |
| 3,821,086 | 6/1974 | Lee et al. | 195/116 |
| 3,868,304 | 2/1975 | Messing | 195/31 F |
| 3,963,788 | 6/1976 | Kruse et al. | 260/635 C |
| 3,963,789 | 6/1976 | Kruse et al. | 260/635 C |
| 3,989,596 | 11/1976 | Long | 195/56 |
| 3,989,597 | 11/1976 | Lee et al. | 195/31 F |
| 3,992,329 | 11/1976 | Eaton et al. | 252/463 |
| 4,083,881 | 4/1978 | Takemura et al. | 260/635 C |

FOREIGN PATENT DOCUMENTS 7675008  6/1976  Japan ..................................... 195/31 F

OTHER PUBLICATIONS

Tsumura et al, "Enzymatic Conversion of D-Glucose to D-Fructose", *Agr. Biol. Chem.*, vol. 25, No. 8, (1961), pp. 616–619.
Pigman et al, *The Carbohydrates*, Academic Press, Inc., New York, (1957), pp. 60–69.
Yamanaka, "Sugar Isomerases", *Agr. Biol. Chem.*, vol. 27, No. 4, (1963), pp. 265–270.
Bilik, "Reactions of Saccharides Catalyzed by Molybdate Ions, II, Epimerization of D-Glucose and D-Mannose", *Chem. Zvest.*, vol. 26, (1972), pp. 183–186.
Takasake et al, "Streptomyces Glucose Isomerase", *Fermentation Advances*, Perlman ed., Academic Press, New York, (1969), pp. 561–589.
Barman, *Enzyme Handbook*, vol. II, Spring-Verlag, New York, (1969), p. 833.

*Primary Examiner*—Thomas G. Wiseman
*Attorney, Agent, or Firm*—Louis F. Kreek, Jr.

[57] ABSTRACT

Mannitol-rich aqueous solutions of sorbitol and mannitol are prepared by a process which includes (1) epimerizing glucose in aqueous solution to obtain an epimerizate containing approximately 30 percent mannose and 70 percent glucose on the dry basis, (2) contacting this glucose-mannose epimerizate with a glucose isomerase enzyme to produce a glucose-fructose-mannose solution, and (3) hydrogenating this glucose-fructose-mannose solution to produce an aqueous solution of sorbitol and mannitol.

11 Claims, No Drawings

HIGH MANNITOL PROCESS (ENZYMATIC ISOMERIZATION)

BACKGROUND OF THE INVENTION

The present invention relates to a process for producing mannitol-rich solutions of sorbitol and mannitol. More particularly, this invention relates to a process for producing a mannitol-rich solution of sorbitol and mannitol from glucose.

It is well known that a mixture of sorbitol and mannitol in aqueous solution can be produced by catalytic hydrogenation of invert sugar, which is an approximately equimolar mixture of glucose and fructose. Invert sugar, in turn, is commonly obtained by inversion of sucrose (ordinary sugar). The yield of mannitol is ordinarily about 24–26 percent by weight, based on total dry solids, when hydrogenation is carried out under neutral or mildly acidic conditions, such as those disclosed in U.S. Pat. No. 2,759,024 to Kasehagen et al. (The theoretical yield of mannitol is about 25 percent by weight of total dry solids, assuming that no isomerization takes place). This yield can be increased by carrying out at least part of the hydrogenation under alkaline conditions, as described in U.S. Pat. Nos. 3,329,729 to Brandner et al., and 3,763,246 to deBerardinis, or by appropriate choice of catalyst, as described in U.S. Pat No. 3,705,199 to deBerardinis, or both. The reaction products obtained according to the processes of these patents contain about 30–36 percent mannitol, about 27–31 percent mannitol, and about 28–29 percent mannitol, all on the dry basis, respectively. In each case the balance of the reaction product is mostly sorbitol.

Enhanced yields of mannitol under alkaline hydrogenation conditions are due to isomerization of part of the glucose present to fructose and mannose. The proportions of glucose, fructose, and mannose in the reaction mixture will vary depending on the alkaline material and the conditions used, and significant quantities of mannose are not ordinarily obtained. Such isomerization is well known in the art, and is discussed, for example, in U.S. Pat. Nos. 3,329,729 and 3,763,246 cited supra, and in Pigman, "The Carbohydrates: Chemistry, Biochemistry, and Physiology," Academic Press, New York, 1957, pages 60–69.

Mannitol may be recovered from aqueous solutions containing both sorbitol and mannitol by fractional crystallization, as described for example in U.S. Pat. No. 3,632,656.

Although enhanced yields of mannitol are obtained under alkaline hydrogenation conditions, the proportion of impurities formed under alkaline hydrogenation conditions is also higher than the proportion formed under neutral or acid hydrogenation conditions. Impurities obtained under alkaline hydrogenation conditions include ethylene glycol, propylene glycol, and glycerine.

Hydrogenation of invert sugar is an attractive commercial route to the production of mannitol when the price of sucrose (ordinary sugar) is low. However, sharp rises and fluctuations in the price of sucrose in recent years have indicated a need for alternate routes.

High costs of mannose and fructose in substantially pure form preclude the economic use of these sugars as starting materials, even though mannose yields essentially pure mannitol and fructose yields a 50:50 mixture of sorbitol and mannitol on catalytic hydrogenation. There is a need for a new process for preparing mannitol which uses an inexpensive starting material and which gives a higher yield of mannitol than present processes.

A process for obtaining sorbitol-mannitol solutions from glucose by first catalytically epimerizing glucose in an acidic usually solution to obtain an epimerizate of glucose and mannose, and then catalytically hydrogenating this epimerizate in an acidic aqueous solution to obtain an aqueous solution of sorbitol and mannitol, is described in my copending U.S. patent application, Ser. No. 578,548, filed May 19, 1975, now U.S. Pat. No. 4,029,878, issued June 14, 1977. Epimerization according to that process is carried out at elevated temperature in an acidic aqueous solution containing at least 50% solids and preferably about 67–70% solids, using a hexavalent molybdenum catalyst such as molybdic acid or an anion exchange resin in the molybdate form. Hydrogenation catalysts and conditions for hydrogenating the glucose-mannose epimerizate to a mixture of sorbitol and mannitol in that process are conventional. Ordinarily the epimerizate will contain about 30% (e.g., about 27–33%) of mannose on the dry basis, and the mol percentage of mannitol in the final product is also usualy about 30%; that is, the mol percentage of mannitol in the final product does not differ significantly from the mol percentage of mannose in the epimerizate.

Epimerization of glucose in aqueous solution into a mixture of glucose and mannose is also described by Bilik in Chem. Zvesti, 26, 183–186 (1972). In Bilik, a 17% (by weight) glucose solution containing 1% by weight of molybdic acids based on glucose, is used, and 25% of the glucose is epimerized to mannose.

The mannose yield obtained in my copending application is significantly higher than that obtained by Bilik. Also, the mannitol yield is significantly higher than those obtained by catalytic hydrogenation of invert sugar under acid or neutral conditions, which as stated above ordinarily yields about 25% mannitol, remainder sorbitol on the dry basis.

Enzymatic isomerization of glucose in aqueous solution to fructose has gained considerable attention in recent years as a means for producing a substitute for sucrose, and there is a considerable volume of patents and other published literature on this subject. Microorganisms of various genera are known to produce glucose isomerase, which is an enzyme capable of isomerizing glucose into fructose. The production and use of glucose isomerase derived from a Pseudomonas microorganism is described in U.S. Pat. No. 2,950,228. An article by Takasaki in "Fermentation Advances," D. Perlman, ed., Academic Press, 1969, pages 561–589, describes the use of glucose isomerase derived from Streptomyces microorganisms, either as a cell-free extract or in the form of heat treated whole cells of Streptomyces microorganisms, for isomerization of glucose to fructose. The enzyme also acts on xylose but not on mannose, arabinose, or ribose, according to Takasaki. The use of Arthrobacter-derived glucose isomerase for the isomerization of glucose to fructose is disclosed in U.S. Pat. Nos. 3,645,848; 3,821,086; 3,989,596; 3,989,597; Re. 29,130; and Re. 29,136. All of these patents except U.S. Pat. No. 3,645,848 disclose the use of flocculated whole Arthrobacter cells containing glucose isomerase. N. Tsumura et al., Agr. Biol. Chem. 25, 1961, pp. 616–619, describe the use of glucose isomerase derived from Aerobacter organisms, while K. Yamanaka, Agr. Biol. Chem. 27, 1963, pp. 265–270, describes the use of glucose isomerase obtained from Lactobacillus organisms. Other glucose isomerase-producing microorganisms are also known. Syrups containing about 40-45 percent by weight of fructose on the dry basis are obtainable by enzymatic isomerization. These syrups are used as sweeteners in various food products.

In carrying out an enzyme-catalyzed isomerization of glucose to fructose, the enzyme may be used in the form of a cell-free extract which is dissolved in the glucose solution, or in an immobilized form in or on a water-insoluble matrix. The matrix may comprise either living or inactivated whole microorganism cells, or may be any other suitable water-insoluble solid support. Takasaki, "Fermentation Advances" cited supra, illustrates both cell-free extracts and glucose isomerase immobilized in whole Streptomyces cells. U.S. Pat. Nos. 3,645,848 and 3,821,086 describe whole Arthrobacter cells containing glucose isomerase. Supports or carriers other than microorganism cells are also known; for example, U.S. Pat. Nos. 3,868,304 and 3,992,329 describe glucose isomerase immobilized on porous inorganic supports. The use of immobilized glucose isomerase is preferred because this permits both continuous column isomerization and repeated use of the enzyme. In contrast, glucose in the form of a cell-free extract can be used only in a batch type reaction and can be used only once, since it is impractical to recover the enzyme.

SUMMARY OF THE INVENTION

A mannitol-rich solution of sorbitol and mannitol is obtained from glucose according to the present invention by (1) catalytically epimerizing glucose in a nonalkaline aqueous solution, thereby obtaining a mixture of glucose and mannose in solution; (2) contacting this mixture of glucose and mannose in aqueous solution with a glucose isomerase enzyme under isomerizing conditions, whereby a portion of the glucose content of the mixture is isomerized and a mixture of glucose, fructose, and mannose in aqueous solution is formed; (3) catalytically hydrogenating this mixture of glucose, mannose and fructose in aqueous solution, thereby forming an aqueous solution containing sorbitol and mannitol.

DESCRIPTION OF THE PREFERRED EMBODIMENT

The first step in the process of this invention is to epimerize glucose catalytically in a non-alkaline and preferably acidic aqueous solution to obtain a mixture of glucose and mannose in aqueous solution. Epimerization is preferably carried out according to the process described and claimed in my copending application Ser. No. 578,548, now Pat. No. 4,029,878 previously cited. According to the process described and claimed in my copending application, an aqueous glucose solution containing at least 50 percent and preferably about 67-70 percent by weight of glucose is epimerized under acidic conditions (pH of about 3-5) at about 70°-160° C., preferably about 90°-130° C., using a hexavalent molybdenum catalyst. The catalyst may be either a hexavalent molybdenum compound, such as molybdic acid, which is dissolved in the glucose solution, or an anion exchange resin in the molybdate form. Strongly basic anion exchange resins are preferred over weakly basis resins. When a dissolved molybdenum catalyst is used, the amount of catalyst is at least about 0.1 percent by weight (as $MoO_3$) (at least about 0.05 percent at temperatures above 110° C.), based on the weight of sugar. Catalyst concentrations of about 0.25 to about 1 percent by weight based on sugar are ordinarily preferred. A particularly preferred procedure is to epimerize glucose in a 67-70 percent aqueous solution which also contains molybdic acid in an amount of about 0.25 percent by weight of molybdenum, based on the initial weight of glucose, and which has a pH of about 3.5 to 4, at a temperature of about 90°-100° C. and at atmospheric pressure until the solution reaches equilibrium. Epimerization may be carried out in an air atmosphere or in an inert atmosphere as desired; results are about the same in either case. An increase in temperature results in shorter reaction time but an increase in by-product formation. The reaction rate decreases at pH above about 4, while pH values below 3.5 and especially below 3 result in oligosaccharide formation. Mannose yields are usually in the range of about 27-33 percent by weight on the dry basis; a mannose yield of about 30 percent on the dry basis is typical. The epimerized glucose (or glucose epimerizate) also contains about 70 percent by weight of unconverted glucose on the dry basis.

Alternatively, one may use the procedure described by V. Bilik in Chem. Svesti, 26, 183-186 (1972) previously cited. Bilik describes a procedure in which a 25 percent yield of mannose at equilibrium is obtained by epimerizing at 90° C. an aqueous solution containing about 17 percent by weight of glucose (i.e., 20 grams of glucose per 100 ml of water) and also containing dissolved molybdic acid in an amount of 1 percent based on glucose (i.e., 200 mg per 100 ml of water). Epimerization according to the process of my earlier application, rather than according to Bilik's process, is preferred because, first, a higher yield of mannose is obtained in my process, and secondly, because the higher solids concentrations used in my process make it unnecessary to evaporate large quantities of water prior to enzymatic isomerization.

The glucose-mannose solution or epimerizate may be treated in order to remove the molybdenum catalyst and other impurities such as color bodies, although such treatment is not necessary since molybdenum does not interfere with enzymatic isomerization of glucose to fructose. The solution can be treated with a cation exchange resin and an anion exchange resin, either simultaneously in a mixed bed resin or consecutively, and with one or more adsorbents, such as an adsorbent resin, activated carbon, or both. The epimerizate solution is preferably diluted with water to a solids content of about 50-55% prior to treatment. A preferred treatment procedure comprises treatment of the diluted epimerizate with a decolorizing resin (e.g., "Duolite S-30"), a strongly acid cation exchange resin, a strongly basic anion exchange resin, a second strongly acid cation exchange resin, a second weakly basic anion exchange resin, and activated carbon (e.g., "Darco S-51") in the order named. The treated solution is essentially neutral, and may have a slightly lower solids content than the untreated solution (say 50% vs. 55% solids) due to the formation of water on neutralization.

Glucose may also be epimerized by contacting an aqueous acidic solution of glucose with a strongly basic anion exchange resin in the molybdate form at elevated temperature, as disclosed in my copending application Ser. No. 578,548, now U.S. Pat. No. 4,029,878. Temperatures of about 90°-100° C. are preferred. Weakly basic anion exchange resins do not give as good results. Molybdate ions can be introduced by conventional ion exchange techniques, i.e., by treating the resin with an aqueous solution of molybdic acid or other hexavalent molybdenum compounds prior to use. Suitable anion exchange resins are well known in the art. The glucose solution is preferably continuously passed slowly, either upwardly or downwardly, through a heated column of the ion exchange resin. The column may be heated by a heating jacket or other means known in the art in order to maintain the desired epimerization temperature. Alternatively, the ion exchange resin can be slurried in the glucose solution and separated after the desired contact time has elapsed. The effluent solution may be purified as described above. The amount of molybdenum in the effluent is ordinarily much less than the amount present when a dissolved molybdenum catalyst is used (although some molybdenum is usually present); consequently, less ion exchange capacity is required.

The next step is to contact the mixture glucose and mannose in aqueous solution with a glucose isomerase enzyme under isomerizing conditions, thereby producing a glucose-fructose-mannose solution. The glucose isomerase may be in any of the physical forms and may be derived from the glucose isomerase-producing microorganisms known in the art. Also, isomerization conditions which are known in the art for isomerization of glucose to fructose may be used in the treatment of glucose-mannose solutions according to this invention.

A particularly preferred procedure is to add water, alkali (e.g., sodium hydroxide) and a water-soluble magnesium salt (e.g., magnesium sulfate or magnesium chloride) to a glucose-mannose solution obtained in the first step in order to adjust the solids content to about 40–60 percent by weight, the pH to about 8.0–8.3, and the magnesium ion concentration to 0.004 M, and then to pass the solution at 60° C. downwardly by gravity through a column containing a packed bed of flocculated Arthrobacter cells which have been prepared in dry form as described in U.S. Pat. No. 3,821,086 and then swelled and conditioned prior to use. A suitable swelling and conditioning procedure is given in Example 1, part B of this specification. The solution may be passed upwardly through the bed if desired. These Arthrobacter cells contain immobilized glucose isomerase enzyme and are in particulate form. The use of Arthrobacter strains NRRL B-3726 and B-3728 is especially preferred. (The strain numbers refer to the numbers assigned by the Northern Regional Research Laboratory of the United States Department of Agriculture, Peoria, Illinois, from which samples of these strains can be obtained). Some drop in pH (typically from about 8.3 to about 7.5) occurs as the solution passes through the enzyme bed. Preferred contact times are such as to cause a conversion of about 40–45 percent of the glucose present to fructose. The mannose content of the solution remains substantially unchanged. The effluent solution obtained from the isomerization column is a solution of glucose, mannose, and fructose.

The isomerization temperature may be from about 60 to about 70° C., preferably about 60° C. Enzyme activity drops off rapidly with decreasing temperature with temperatures below 60° C. while increases in temperature from about 70° to about 80° results in substantially increased by-product formation (e.g., color bodies and psicose) without any significant increase in enzyme activity. (Enzyme activity decreases rapidly if the temperature is increased above 80° C.). The solution pH can also be varied from the preferred values indicated; the initial pH can range from about 7 to 8.5.

Advantages of Arthrobacter-derived isomerase over glucose isomerase derived from other genera of microorganism include the following: (1) whole microorganism cells can be used without heat treatment, (2) substantial glucose isomerase activity is retained even after long use, and (3) the enzyme is activated with magnesium alone, rather than with both magnesium and cobalt, as is the case with most other glucose isomerase enzymes.

Although Arthrobacter is a preferred glucose isomerase producing microorganism for use in the present invention, it is understood that glucose isomerase produced by other genera of microorganisms can be used if desired. Examples of such other genera have been cited previously in this specification. For example, whole cells of certain strains of Streptomyces such as *Streptomyces albus* as described in Takasaki, "Fermentation Advances" cited supra, can be used. Streptomyces cells, unlike Arthrobacter cells, must be heat treated (at 60° C. or slightly higher) in order to stabilize the glucose isomerase content.

Good results can also be obtained by passing a glucose-mannose solution through a column of glucose isomerase immobilized on a water-insoluble solid support, such as porous alumina as described in U.S. Pat. No. 3,868,304. A cell-free extract of glucose isomerase, dissolved in the glucose-mannose epimerizate solution, can be used but is not desirable because recovery of the enzyme is costly and uneconomical. A water-insoluble form of the enzyme is preferred.

Suitable isomerization conditions are well known in the art. These vary somewhat from microorganism to microorganism, but typically the solution prior to isomerization has a temperature of about 60–70° C. (which is kept constant throughout isomerization), and a pH of about 6.5 to 9 and more usually about 7 to about 8.5, depending on the microorganism chosen. Also, as known in the art, small amounts of magnesium (usually as magnesium sulfate) and cobalt (typically as cobalt sulfate or chloride) are dissolved in this solution in order to activate the enzyme. (As previously explained, no cobalt is required for activation of an Arthrobacter-derived glucose isomerase).

The isomerization effluent solution may be purified, as for example by contact with activated carbon and with anion and cation exchange resins, as is known in the art. Treatment to remove molybdenum is essential if the molybdenum from the epimerization step has not been removed previously, since molybdenum may poison the hydrogenation catalyst. If the isomerization effluent does not contain molybdenum, purification may be omitted.

The third and final step in the present process is to hydrogenate catalytically the solution of glucose, mannose, and fructose obtained on enzymatic isomerization. This solution has preferably been treated with activated carbon and with anion and cation exchange resins. Catalytic hydrogenation is preferably carried out using catalysts and reaction conditions which are known in the art. The preferred catalysts are supported nickel catalysts (e.g., nickel on kieselguhr) such as those described in U.S. Pat. No. 3,705,199; other nickel catalysts such as Raney nickel can also be used. Alternatively, supported ruthenium catalysts, such as those described in U.S. Pat. No. 3,963,788 and 3,963,789 to Leon W. Wright and myself, can be used. Hydrogenation is carried out at superatmospheric pressures, usually at least 100 psig. and more usually from about 1,000 to about 3,000 psig. Hydrogenation temperatures of about 100 to about 160° C. are ordinarily preferred. As is known in the art, higher temperatures give shorter reaction times. A wide range of solution concentrations may be used for hydrogenation; concentrations of about 67-70 percent by weight of sugar (glucose+fructose+mannose) are preferred, and the solution from the isomerization step may be concentrated, as for example by evaporation of part of the water content, in order to achieve this concentration. Either batch, semicontinuous, or continuous hydrogenation may be used. The preferred pH for hydrogenation is from mildly acidic to neutral (e.g., from about 3 to about 7); under these conditions no appreciable isomerization of the sugars takes place during hydrogenation. As a result, the glucose content of the solution is converted substantially to sorbitol, the mannose content is converted substantially to mannitol, and the fructose content is converted to approximately equimolar portions of sorbitol and mannitol. The mannitol content of the product solution will ordinarily be about 40 percent by weight on the dry basis, although it may be slightly greater or slightly less. The product contains only small amounts of impurities.

Alkaline hydrogenation conditions can be used if desired. Although the use of alkaline conditions enhances the yield of mannitol somewhat, the amount of by-products is substantially greater than when hydrogenation is carried out under acid or neutral conditions.

Mannitol can be separated from sorbitol and recovered by means known in the art.

It is necessary to carry out epimerization before enzymatic isomerization rather than afterward, in order to get optimum mannitol yields. If glucose is enzymatically isomerized to a mixture of glucose and fructose and this is contacted with a molybdenum catalyst under epimerization conditions, quantities of mannose in the resulting glucose-fructose-mannose mixture, and quantities of mannitol in the sorbitol-mannitol mixture obtained on hydrogenation, are significantly lower than when the sequence of steps of this invention is followed.

The present process has several advantages over previous processes for obtaining mannitol in admixture with sorbitol. First of all, glucose is used as the starting material, so that the cost is not subject to the vagaries in the price of sucrose. Secondly, the yield of mannitol is greater than the yield of mannitol obtained by hydrogenation of invert sugar under acid or neutral conditions, and the by-product content is substantially lower than the by-product content obtained when invert sugar is hydrogenated under alkaline conditions. Furthermore, the yield of mannitol obtained in the present process is substantially higher than the yield according to the process of my copending application Ser. No. 578,548 or in other process which start from glucose but which do not utilize the enzymatic isomerization of the glucose-mannose epimerizate. Both high mannitol yields and the low by-product quantities, a combination not readily achieved, are obtained in the present process.

This invention will now be described in further detail with reference to the following examples.

EXAMPLE 1

A. Epimerization

Glucose is epimerized into a mixture of glucose and mannose as follows: An aqueous glucose solution, containing approximately 70-74% by weight of glucose, is heated to 95° C., molybdic acid (0.25% by weight of Mo, based on the weight of glucose) is added, and the temperature is maintained at about 95°-96° C. for 3 hours. The solution is cooled, diluted with water to 60% by weight solids, and treated with anion and cation exchange resins. Three solutions of epimerized glucose, prepared in the foregoing manner, are pooled, further treated with anion and cation exchange resins, and then treated with activated carbon (0.25% by weight of "Darco S-51", based on the weight of sugar). Analysis of the treated solution shows 44.7% by weight of water (i.e., 55.3% by weight of solids), with a solids content (in percent by weight, dry basis) of 28.9% mannose and 69.3% glucose.

B. Enzymatic Isomerization

A column of swelled and conditioned flocculated whole Arthrobacter cells containing immobilized glucose isomerase is prepared as follows: First, the Arthrobacter cells are flocculated, dewatered, extruded and dried as described in U.S. Pat. No. 3,821,086. The dried cells are in pellet form. The dried cells are swelled and conditioned as follows: 75 grams of dried cells are weighed into 800 ml of an aqueous solution of 0.1 M $NaHCO_3$+0.01 M $MgCl_2$. The resulting cell slurry is stirred and allowed to stand for 30 minutes. The cells swell to about 320 ml. A column, 3 feet high × 1.5 inches in diameter, is half filled with an aqueous solution of 0.05 M $NaHCO_3$+0.01 M $MgCl_2$, and the swelled cells are poured into the column. The cells are washed for 4 hours at the rate of 300 ml/hr with an aqueous solution of 0.05 M $NaHCO_3$+0.01 M $MgCl_2$, and are then washed for 30 minutes with an aqueous 0.004 M $MgCl_2$ solution. The column is then ready for introduction of glucose epimerizate solution.

Glucose epimerizate, obtained and purified in part A of this example, is diluted with water to a solids concentration of 50 percent by weight. Magnesium chloride is added to obtain a concentration of 0.004 M, and the pH of the solution is adjusted to 8.3 by addition of 20 percent NaOH. Seven liters of the solution are passed downwardly at a rate of 3 ml/min through a column containing 75 grams (dry basis) of conditioned and swelled flocculated, dewatered whole Arthrobacter cells containing glucose isomerase, prepared as described above. The cell bed in the column is 8 inches high and 1.5 inches in diameter. The column is maintained at a temperature of 60° C. An effluent solution of light brownish color is collected. This solution is decolorized by treatment with a mixed bed resin (an anion exchange resin and a cation exchange resin) and with decolorizing carbon (Darco S-51).

Six portions of effluent are collected and two are analyzed by gas-liquid chromatograph (GLC) for mannose, fructose, and glucose. Results are given in Table 1 below. All amounts shown are in percent by weight on the dry basis.

TABLE I

| Portion No. | Percent by weight (dry basis) | | |
|---|---|---|---|
| | Mannose | Fructose | Glucose |
| 1 | 28.7 | 21.3 | 46.1 |
| 6 | 31.0 | 17.9 | 47.7 |

C. Hydrogenation 224 grams of epimerized and enzymed treated glucose solution (123 grams of solids), treated as described in part B of this example and containing 28.7 percent by weight mannose, 21.3 percent fructose, and 46.1 percent glucose, all by weight on the dry basis, are charged to an autoclave. Also charged to the autoclave are 5 grams of catalyst of nickel supported on kieselguhr. Also charged to the autoclave are 25 ml of water, giving a solution having a solids content of 50 percent by weight. The initial pH of this sugar solution is 6.1. The autoclave contents are flushed with nitrogen, pressured with hydrogen to 1525 psig., heated to 150° C. and 1775 psig., and maintained at this temperature for 1 hour. The autoclave pressure drops to 1700; psig. after five minutes and to 1690 psig. after 20 minutes, remaining constant thereafter. This indicates that the reaction was complete in 20 minutes or less. After one hour, the autoclave contents are cooled to room temperature and 1225 psig. The final pH of the solution is 5.4. The catalyst was separated from the solution by filtration. The filtrate, which is water white, is treated with mixed bed ion exchanged resins and with carbon, and is concentrated to approximately 55 percent solids. Analysis of the solution on the dry basis (average of two samples) shows approximately 42 percent by weight of mannitol based on the total weight of hexitols in the reaction product.

EXAMPLE 2

A. Epimerization

An aqueous glucose solution (about 69 percent by weight glucose) is epimerized as described in Example 1, but is not treated with ion exchange resins or with carbon, so that the molybdenum catalyst remains in solution. The glucose epimerizate has a solids content of about 69 percent by weight and contains 25.5 percent by weight of mannose and 71.2 percent by weight of glucose on the dry basis.

B. Enzymatic Isomerization

Glucose epimerizate obtained in part A of this example is diluted to 50 percent by weight solids, adjusted to pH 8.3, and treated with magnesium chloride (to 0.004 M) and passed through a bed of whole flocculated and dewatered Arthrobacter cells at 60° C. and the rate of 3 ml/min. The cells are swelled as described in Example 1, part B prior to use. Three liters of the treated solution are passed through a column of whole Arthrobacter cells and treated with resin and carbon according to the procedure of Example 1, part B.

C. Hydrogenation

The purified effluent solution obtained in part B of this example is catalytically hydrogenated as described in example 1, part C, yielding a reaction product containing 40.8 percent by weight mannitol on the dry basis.

A major advantage of the present process is that yields of mannitol are ordinarily 40 percent by weight or higher on the dry basis. This is significantly better than the yields obtained in most presently known processes that are based on either glucose or sucrose (or invert sugar) as the starting material. At the same time, volatile by-product formation in the present process is quite low, so that the present process represents a distinct improvement over processes in which mannitol yield is increased at the expense of by-product formation by carrying out hydrogenation under alkaline conditions. In short, the present process offers a unique combination of high mannitol yield and low volatile by-product formation which has not been achieved heretofore.

What is claimed is:

1. A process for obtaining a mannitol-rich solution of sorbitol and mannitol from glucose which comprises:
   (a) catalytically epimerizing glucose in an acidic aqueous solution in the presence of a hexa- valent molybdenum catalyst at a temperature not exceeding about 100° C., thereby obtaining a mixture of glucose and mannose in aqueous solution;
   (b) contacting said mixture of glucose and mannose in aqueous solution with a glucose isomerase enzyme under enzymatic isomerization conditions, whereby a portion of the glucose content of said mixture is isomerized and a mixture of glucose, fructose, and mannose in aqueous solution is formed; and
   (c) catalytically hydrogenating said mixture of glucose, fructose, and mannose in aqueous solution, thereby forming an aqueous solution containing sorbitol and mannitol.

2. A process according to claim 1 in which said glucose is epimerized at a temperature of about 90°–100° C.

3. A process according to claim 2 in which said hexavalent molybdenum catalyst is molybdic acid.

4. A process according to claim 1 in which said mixture of glucose and mannose in aqueous solution is passed through a column of whole Arthrobacter cells containing said glucose isomerase enzyme.

5. A process according to claim 1 in which said mixture of glucose, fructose and mannose is catalytically hydrogenated under non-alkaline conditions.

6. A process according to claim 1 in which said mixture of glucose, fructose, and mannose is hydrogenated in the presence of a nickel catalyst.

7. A process according to claim 1 in which: said glucose is epimerized in an acidic solution, (a) said mixture of glucose and mannose in aqueous solution is passed through a column of whole Arthrobacter cells containing said glucose isomerase enzyme, and (b) said mixture of glucose, fructose, and mannose is hydrogenated under non-alkaline conditions in the presence of a nickel catalyst.

8. A process according to claim 7 in which said hexavalent molybdenum catalyst is dissolved in said acidic solution.

9. A process according to claim 7 in which said mixture of glucose and mannose is treated with an ion exchange resin prior to contact with said Arthrobacter cells in order to remove said molybdenum catalyst.

10. A process for obtaining a mixture of glucose, fructose, and mannose in aqueous solution which comprises:
    (a) catalytically epimerizing glucose in an acidic aqueous solution in the presence of a hexavalent molybdenum catalyst at a temperature not exceeding about 100° C., thereby obtaining a mixture of glucose and mannose in aqueous solution; and
    (b) contacting said mixture of glucose and mannose in aqueous solution with a glucose isomerase enzyme under enzymatic isomerization conditions, whereby a portion of the glucose content but no substantial portion of the mannose content of said mixture is isomerized and a mixture of glucose, fructose, and mannose in aqueous solution is formed.

11. A process according to claim 10 in which said glucose is epimerized at a temperature of about 90°–100° C.

* * * * *

UNITED STATES PATENT AND TRADEMARK OFFICE
CERTIFICATE OF CORRECTION

PATENT NO. : 4,173,514
DATED : November 6, 1979
INVENTOR(S) : Walter M. Kruse

It is certified that error appears in the above-identified patent and that said Letters Patent are hereby corrected as shown below:

Column 1, lines 54 to 57, cancel all matter following the period in line 54 after conditions.

Column 3, line 18, add "cited supra" after 3,821,086.

Column 4, line 25 "Svesti" should read --Zvesti--.

Column 6, lines 36 and 37 delete "(which is kept constant throughout isomerization),".

Column 8, line 57, "chromatograph" should read --chromatography--

Column 10, lines 35 and 36, delete "said glucose is epimerized in an acidic solution,".

Signed and Sealed this

Eighteenth Day of March 1980

[SEAL]

Attest:

Attesting Officer

SIDNEY A. DIAMOND

Commissioner of Patents and Trademarks